United States Patent
McShane et al.

(10) Patent No.: US 7,230,014 B1
(45) Date of Patent: Jun. 12, 2007

(54) PHARMACEUTICAL FORMULATION COMPRISING GLYCINE AS A STABILIZER

(75) Inventors: James McShane, Wake Forest, NC (US); Ray Wood, Raleigh, NC (US); Sumio Watanabe, Aichi (JP); Kiyoshi Iwamoto, Kagamihara (JP); Katsumi Onai, Aichi (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/549,858

(22) Filed: Apr. 14, 2000

Related U.S. Application Data

(63) Continuation of application No. PCT/US98/21972, filed on Sep. 14, 1998.
(60) Provisional application No. 60/062,089, filed on Oct. 14, 1997.

(51) Int. Cl.
*A61K 31/44* (2006.01)

(52) U.S. Cl. .................. 514/338; 514/339; 514/340; 514/556; 514/557

(58) Field of Classification Search .............. 514/338, 514/339, 340, 556, 557
See application file for complete search history.

(56) References Cited

U.S. PATENT DOCUMENTS

| | | | |
|---|---|---|---|
| 4,255,431 A | 3/1981 | Junggren et al. | 424/267 |
| 4,265,888 A | 5/1981 | Kagitani et al. | 424/233 |
| 4,337,257 A | 6/1982 | Junggren et al. | 424/263 |
| 4,508,905 A | 4/1985 | Junggren et al. | 546/271 |
| 5,045,552 A * | 9/1991 | Souda et al. | 514/338 |
| 5,536,735 A * | 7/1996 | Takechi et al. | 514/338 |

FOREIGN PATENT DOCUMENTS

| | | |
|---|---|---|
| EP | 0 074 341 | 3/1983 |
| EP | 0 082 481 | 6/1983 |
| EP | 0 167 943 | 1/1986 |
| EP | 0 173 664 | 3/1986 |
| EP | 0 268 956 | 6/1988 |
| GB | 2134523 | 8/1984 |
| JP | 56-065816 | 6/1981 |
| JP | H5-194225 | 8/1993 |
| WO | 95/28951 | 11/1995 |

OTHER PUBLICATIONS

Osol, A. et al., Editor–in–Chief of Remington's Pharmaceutical Sciences, 15th Edition, p. 963, Jun. 11, 1976.*

* cited by examiner

*Primary Examiner*—Dwayne C. Jones
(74) *Attorney, Agent, or Firm*—Wilmer Cutler Pickering Hale and Dorr LLP

(57) ABSTRACT

The present invention provides pharmaceutical formulations suitable for intravenous injection comprising a lyophilized anti-ulcerative agent reconstituted in isotonic solutions suitable for intravenous administration, such as 5% dextrose or 0.9% sodium chloride. The solutions are brought to a pH of between about 9 and about 12, preferably between about pH 10 and 11, by a glycine-sodium hydroxide buffer. Such formulations are chemically and physically stable, and do not significantly change color, for at least between about 6 and about 12 hours at room temperature, and are stable to color change for from between about 24 and 48 hours if kept at 5° C.

5 Claims, 5 Drawing Sheets

PHARMACEUTICAL FORMULATION COMPRISING GLYCINE AS A STABILIZER

This is a continuation of International Application No. PCT/US98/21972, filed Sep. 14, 1998, which claims priority under 35 U.S.C. §119(e) of provisional application serial No. 60/062,089 filed Oct. 14, 1997. The entire disclosure of both of these applications is hereby incorporated by reference.

FIELD OF THE INVENTION

This present invention relates to the preparation of pharmaceutical formulations with anti-ulcerative properties, and in particular, formulations that are reconstituted for intravenous administration.

BACKGROUND OF THE INVENTION

Souda et al., U.S. Pat. No. 5,045,552, incorporated by reference herein, describes compounds that inhibit an $H^+/K^+$-ATPase present in the stomach. These compounds are useful for treatment of peptic ulcers and other disorders associated with secretion of gastric acid, such as heartburn and gastroesophageal reflux. For example, one such compound has the following structure:

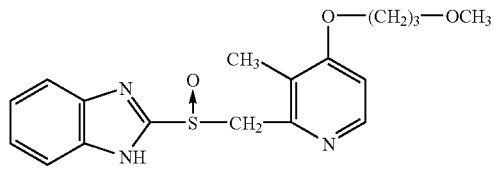

and includes pharmaceutically acceptable salts of the compound. This compound is referred to herein as Compound 1.

It is desirable when preparing reconstituted solutions of such anti-ulcerative compounds that are suitable for intravenous administration, that the solubilized compounds exhibit physical and chemical stability for at least between about 6 and about 12 hours at room temperature. It has been found by the present inventors that anti-ulcerative compounds such as Compound 1 and the compounds described by general formula I below discolor when they are reconstituted, i.e., dissolved, in aqueous solutions, particularly in solutions suitable for intravenous administration, e.g., 5% dextrose or 0.9% saline. Such solutions quickly turn yellow to yellow-brown.

The compounds of the present invention have been determined to be more potent $H^+/K^+$-ATPase inhibitors than omeprazole sodium. However, in order to provide clinically useful pharmaceutical formulations of the compounds disclosed herein for intravenous administration, it is first necessary to provide formulations for lyophilization and intravenous administration that do not degrade physically, chemically and/or demonstrate a change in color.

DETAILED DESCRIPTION OF THE INVENTION

Figure 1:
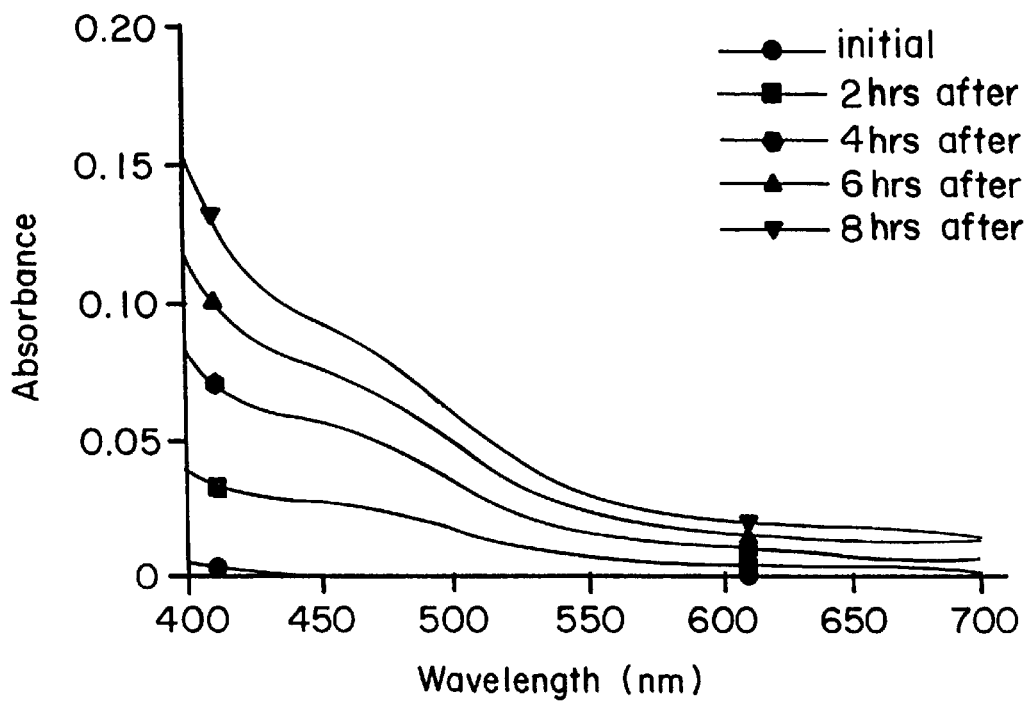
FIG. 1 is a graph showing the changes in absorption spectrum of compound 1 at a concentration of 4 mg/ml in 0.9% saline at pH 10 as a function of time after dissolution, with storage at room temperature (25° C.) in the dark.

All patents, patent applications, and publications cited in this application are incorporated by reference in their entirety. In the case of a conflict of disclosure, the present specification is controlling.

It has now been surprisingly and unexpectedly discovered that if lyophilized compounds of general formula I below are reconstituted in isotonic solutions suitable for intravenous administration, such as 5% dextrose or 0.9% sodium chloride, that have been brought to a pH of between about 9 and about 12, preferably between about pH 10 and 11, by a glycine-sodium hydroxide buffer, such formulations are chemically and physically stable, and do not significantly change color, for at least between about 6 and about 12 hours at room temperature. It was also discovered that the compounds dissolved in such isotonic solutions are stable to color change for from between about 24 and 48 hours if kept at 5° C. It has also been discovered that the use of glycine buffers with a pH of between about 9 and about 12, preferably between about pH 10 and 11, is beneficial in preparing lyophilized samples of the compounds of the invention.

Thus, the present invention provides pharmaceutical formulations suitable for intravenous injection comprising an anti-ulcerative agent having the following general formula:

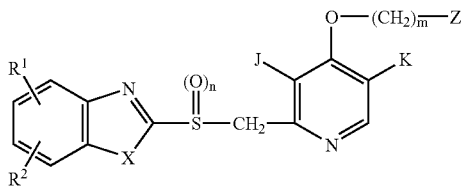

where

R[1] and R[2] are, independently, hydrogen, lower alkyl, lower alkoxy, halogenated lower alkyl, lower alkoxycarbonyl or carboxyl group or a halogen atom;

X is O, S or

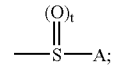

(in which R[3] stands for a hydrogen atom or a lower alkyl, phenyl, benzyl or lower alkoxycarbonyl group); and Z is selected from:

(1) a group of the formula:

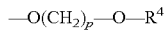

where p is an integer of 1 to 3 and R[4] is a hydrogen atom or a lower, aryl or aralkyl group;

(2) a group of the general formula:

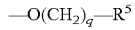

where q is an integer of 1 to 3 and R[5] is a halogen atom or an alkoxycarbonyl, aryl or heteroaryl group;

(3) a group of the general formula:

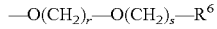

where r and s each independently are an integer of 1 to 5 and R[6] is a hydrogen atom or a lower alkyl group;

(4) a group of the formula:

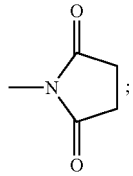

(5) a group of the formula:

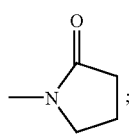

(6) a group of the formula:

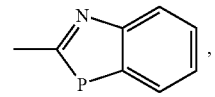

(7) a group of the general formula:

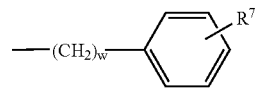

where t is an integer of 0 to 2 and A is a lower alkyl, alkoxycarbonylmethyl, pyridyl or furyl group, or a group of the general formula:

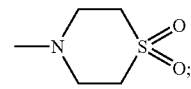

where P is selected from the group consisting of: —NH—, —O— or —S—; or a group of the general formula:

wherein R[7] is hydrogen or lower alkyl and w is from 0 to 3;

(8) a group of the general formula:

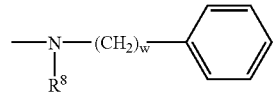

where R[8] is an acetoxy or lower alkyl group; and (9) a group of the general formula: —OR[9] where R[9] is a hydrogen atom or a lower alkyl or aryl group;

n is an integer of 0 to 2; m is an integer of 2 to 10, and J and K are independently hydrogen or lower alkyl, with the proviso that when Z is a group falling under the above category (9), R[9] is a lower alkyl group and m stands for an integer of 3 to 10, and pharmaceutically acceptable salts thereof.

The pharmaceutical formulations also contain a glycine-sodium hydroxide buffer system, and an agent that imparts tonicity to the formulation (a "tonicity agent"). Such agents are well-known in the art, and include sodium chloride, dextrose, mannitol, glycerin, sucrose and lactose. Isotonic solutions posses the same osmotic pressure as blood plasma, and so can be intravenously infused into a subject without changing the osmotic pressure of the subject's blood plasma.

The definitions for R[1], R[2], X, n, J, K, Z and m are used consistently throughout the specification that follows and in the appended claims.

In the definition of the compounds of general formula (I), the lower alkyl group defined above with respect to R[1], R[2], R[3], R[4], R[6], A, R[7], R[8], J, and K in compound (I) of the present invention may be straight-chain or branched alkyl groups having 1 to 6 carbon atoms. Examples include methyl, ethyl, n-propyl, n-butyl, isopropyl, isobutyl, 1-methylpropyl, tert-butyl, n-pentyl, 1-ethylpropyl, isoamyl, n-hexyl groups, and the like, among which methyl and ethyl groups are most preferred.

The lower alkoxy group and the lower alkoxy moiety of the lower alkoxycarbonyl group defined above with respect to $R^1$ and $R^2$ may be an alkoxy group derived form the above-defined and exemplified lower alkyl group. Methoxy and ethoxy groups are most preferred alkoxy groups.

The halogen atom defined above includes chlorine, bromine, iodine or fluorine. The aryl group defined above with respect to $R^4$ and $R^5$ may be, e.g., phenyl, tolyl, xylyl, naphthyl or the like which may be substituted with a lower alkoxy or hydroxyl group, a halogen atom or the like.

Examples of the arylalkyl defined above with respect to $R^4$ include benzyl and phenethyl groups.

Examples of the heteroaryl group defined above with respect to $R^5$ include pyridyl, furyl, and thienyl groups.

In the definition of Z in general formula (I), groups (1), (2), (3), (4), (5) and (9) are preferred; group (9) is the most preferred. $R^1$ and $R^2$ are preferably both hydrogen; another preferred configuration of $R^1$ and $R^2$ is when $R^1$ is lower alkyl, e.g., methyl, and $R^2$ is hydrogen. X is preferably $-NR^3$ where $R^3$ is hydrogen. A preferred value for n is 1. The preferred substituents for J and K are both hydrogen or, where J is lower alkyl, e.g. methyl, K is preferably hydrogen, and when J is hydrogen K is preferably lower alkyl, e.g. methyl. Thus, J or K are independently preferably hydrogen or methyl, most preferably J is methyl and K is hydrogen.

A first preferred class of compounds included in the pharmaceutical formulations of the present invention fall within the compounds of general formula (I) are represented by the following formula (A):

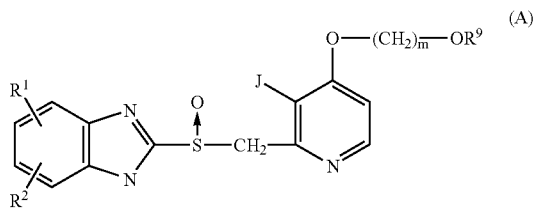

where $R^1$ and $R^2$ are independently selected from the group consisting of hydrogen, lower alkyl, lower alkoxy, halogenated lower alkyl, lower alkoxycarbonyl, a carboxyl group, and halogen; $R^9$ is selected from the group consisting of hydrogen, lower alkyl, and aryl; J is selected from the group consisting of hydrogen or lower alkyl; m is an integer from 2 to 10; and pharmaceutically acceptable salts thereof. In formula A, it is preferred that $R^1$ and $R^2$ are both hydrogen; also preferred is when $R^1$ is 5-lower alkoxy, 5-lower alkyl or 5-halogenated lower alkyl and $R^2$ is hydrogen. Preferred substituents at J are hydrogen or methyl; preferred values of m are from 3 to 10, the most preferred being 3; and the preferred $R^9$ substituents are lower alkyl or aryl. Most preferred at $R^9$ is methyl.

In one group of preferred compounds of formula A, $R^1$ and $R^2$ are both hydrogen, J is methyl, m is 3 and $R^9$ is methyl.

In a second group of preferred compounds falling within formula A, $R^1$ and $R^2$ are both hydrogen, J is hydrogen, m is 3 and $R^9$ is methyl.

In a third group of preferred compounds falling within formula A, $R^1$ and $R^2$ are both hydrogen, J is methyl, m is 2 and $R^9$ is benzyl.

A second class of compounds falling within general formula (I) for inclusion in the pharmaceutical formulations of the present invention are represented by formula (B), as follows:

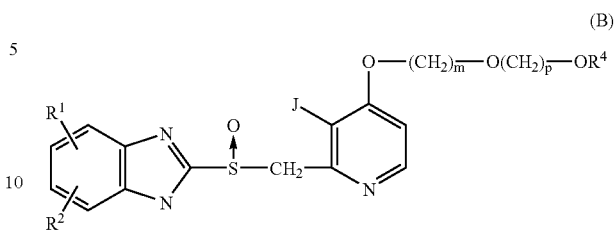

where $R^1$ and $R^2$ are independently selected from the group consisting of hydrogen, lower alkyl, lower alkoxy, halogenated lower alkyl, lower alkoxycarbonyl, a carboxyl group, and halogen; $R^4$ is selected from the group consisting of hydrogen, lower alkyl, aryl, and aralkyl; J is selected from the group consisting of hydrogen or lower alkyl; m is an integer from 2 to 10; p is an integer from 1 to 3; and pharmaceutically acceptable salts thereof.

In compounds of formula (B), the preferred substituents for $R^1$ and $R^2$ are both hydrogen; also preferred are compounds where $R^1$ is 5-lower alkoxy, 5-lower alkyl or 5-halogenated lower alkyl and $R^2$ is hydrogen. Preferred values of m are 2 or 3; preferred values of p are 2 or 3; and the preferred substituents at $R^4$ are methyl or benzyl. Most preferred are compounds of formula (B) where $R^1$ is 5-methyl, $R^2$ is hydrogen, J is methyl, m is 2, p is 2 and $R^4$ is methyl.

Examples of the pharmaceutically acceptable salts include salts of inorganic acids, such as hydrochloride, hydrobromide, sulfate and phosphate; those with organic acids, such as acetate, maleate, tartrate, methanesulfonate, benzenesulfonate, and toluenesulfonate; and those with amino acids such as arginine, aspartic acid and glutamic acid.

Some of the compounds according to the present invention can form a salt with a metal such as Na, K, Ca or Mg. These metal salts are also included among the pharmaceutically acceptable salts of the present invention. For example, compounds represented by the general formula (I), wherein X is a group of

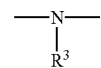

and $R^3$ is a hydrogen atom, or compounds represented by the general formula (I), where Z is a group of category (7) and B is an NH group, can be present as a metal salt.

The compounds of the present invention also can take the form of hydrates, prodrugs, or stereoisomers. It will be appreciated by those of ordinary skill in the art that variations and obvious modifications can be made to the presently claimed invention, said variations and modifications being within the scope of the claimed invention.

Methods for the preparation of the compounds of the stabilized formulations of the invention are disclosed in Souda et al., U.S. Pat. 5,045,552.

The present invention also provides methods for the stabilization of compounds of general formula I above, both in the course of preparing lyophilized samples for reconstitution, and in reconstituted formulations suitable for intravenous administration. Prior to the present invention, the utility of glycine as a color stabilizer for solutions of the compounds of the invention was not known in the art, either in the context of preparing solutions for lyophilization, or for preparing solutions for intravenous administration.

To prepare lyophilized samples for reconstitution, a desired quantity of a compound of the invention is dissolved in a sufficient amount of an aqueous solution (i.e., an amount of solution in which the compound will completely dissolve) which also comprises a glycine-sodium hydroxide buffer such that the pH of the solution is between about 9 and 12, preferably between about pH 10 and about 11. The concentration of glycine in the solution is between about 1 and 300 mM, preferably between about 10 and about 150 mM. The concentration of compound in such solutions is generally from between about 1 mg/ml and 50 mg/ml. The solution is then lyophilized in a sealable container, such as a vial, and the container is sealed such that exchange of air between the inside of the sealable container and the external environment of the container is not possible. The container will typically contain between about 1 and 100 mg of compound, preferably between about 20 and 60 mg of compound, and most preferably about 40 mg of compound.

According to the present invention, reconstituted solutions for intravenous administration can be prepared by initially dissolving an amount of a desired lyophilized compound (plus any other solutes, such as glycine-NaOH buffer, which were lyophilized with the compound) in a sufficient amount of a sterile, aqueous solution to completely dissolve the lyophilized compound. Such initially dissolved solutions contain the original glycine-NaOH buffer system, substantially undiluted, and have a pH of from between about 10 and about 11.5. Under these conditions, as determined by the present inventors, the anti-ulcerative compounds of the invention are chemically and physically stable.

In order to deliver the compounds of the present invention intravenously, they may be dissolved in sterile solutions suitable for intravenous administration, such as normal saline (0.9% saline) or 5% dextrose. Such solutions typically have a pH of between about 4 and about 5, respectively. When the residual glycine-NaOH buffer system is diluted in the solution suitable for intravenous administration, for example a 50-fold dilution of 2 ml of a 20 mg/ml initial solution of anti-ulceratiye compound, the pH of the resulting solution falls below the pH 9 to 12 range in which the anti-ulcerative compounds are most stable. Thus, according to the present invention, additional glycine-NaOH can be added to or included in the ultimate solution to be intravenously administered. The concentration of glycine-NaOH buffer in the final solution for intravenous administration should be between about 1 mM and 300 mM, preferably between about 10 mM and 150 mM, more preferably between 10 and 50 mM and most preferably between about 10 mM and 25 mM. The pH of the resulting solution should be alkaline, preferably between about pH 9 and 12, most preferably between pH 10 and 11.

The present invention is illustrated by the following examples, which are intended merely to illustrate the invention and not to limit its scope.

EXAMPLE 1
pH Studies

The chemical and physical stability of compound 1 at 8 mg/ml in a water for injection (WFI), adjusted with dilute (6 N) NaOH to pH 9.5, 10, 11, and 11.5, was evaluated at room temperature, 5° C., and −20° C. Chemical stability was monitored by evaluating the residual potency and impurity levels over 48 hours by HPLC. Physical stability was evaluated by measuring the rate of color formation at 405 nm and by visual observations.

The order of chemical and physical stability is pH11.5>pH11>pH10.5>pH10>pH9.5 at 5° C. and room temperature. That is, chemical and physical stability of compound 1 is highest at pH 11.5, and decreases with pH; this effect is found at room temperature and at reduced temperatures. Solutions at pH 9.5 began to assume a yellow color within 30 minutes; the color intensified rapidly. At room temperature, solutions at pH 10.5 were marginally stable at 24 hours with regard to chemical and physical stability; however, at cold temperatures (5° C.), pH 10.5 was found to be adequate for 24 hours stability.

At pH 11 or greater and in cold temperatures, solutions of compound 1 appear to be adequately stable for the manufacture and handling in preparation for freeze drying. It was concluded that pH levels below 10.5 should be avoided.

EXAMPLE 2
Preliminary Buffer Evaluation

It is desirable that the pH of solutions of compound 1 and other compounds of the invention in 5% dextrose or normal saline remain in a range near about pH 10 to provide for an acceptable use period in a clinical setting. Phosphate and glycine buffer systems were tested. Phosphate was found to be an effective buffer in tie desired pH range, but, as indicated below, precipitated during freeze-drying of samples containing it; glycine-NaOH was an effective buffer and had a stabilizing effect on color change and may affect turbidity when evaluated with compound 1.

Solutions of compound 1 in 50 mM phosphate buffer behaved similarly with regard to color formation as unbuffered compound 1 solutions (i.e., color formation was not inhibited). In 100 mM glycine/NaOH at pH values above 10, discoloration was substantially slower. Freeze-drying of compound 1 solutions in phosphate and glycine buffers yielded white, well-formed plugs. Reconstitution of the phosphate-containing plugs produced hazy solutions, i.e., precipitation. Based on this propensity to precipitate, phosphate was disqualified as a buffer for the compounds of the invention.

EXAMPLE 3
Glycine Concentration and Temperature Studies

Compound 1 at 8 mg/ml in glycine at 0 mM, 100 mM, and 150 mM were evaluated at pH 10.5 to 11 at room temperature, 5° C., and −20° C. Chemical stability was monitored by measuring the residual potency and impurity levels over 48 hours. Physical stability was evaluated by measuring the rate of color formation at 405 nm and by visual observations. The results for color formation are shown in Tables 1, 2, and 3, below. A, B, and C contain 7.5 mg/ml glycine, equal to 100 mM glycine. D and E have 11.25 mg/ml glycine, equal to 150 mM glycine. F is the control without glycine. The pH of the solution is indicated in parentheses; the values in the tables are the absorbance at 405 nm.

TABLE 1

COLOR INFORMATION
ROOM TEMPERATURE (25° C.) SAMPLES
(ABSORBANCE AT 405 nm)

| | A(11.0) | B(10.76) | C(10.5) | D(11.0) | E(10.5) | F(10.5) |
|---|---|---|---|---|---|---|
| 0 hours | 0.009 | 0.010 | 0.011 | 0.008 | 0.011 | 0.012 |
| 6 hours | 0.034 | 0.048 | 0.066 | 0.032 | 0.056 | 0.188 |
| 12 hours | 0.053 | 0.076 | 0.107 | 0.047 | 0.089 | 0.349 |
| 24 hours | 0.101 | 0.145 | 0.200 | 0.091 | 0.162 | 0.838 |
| 48 hours | 0.163 | 0.245 | 0.333 | 0.152 | 0.269 | 2.396 |

TABLE 2

REFRIGERATED SAMPLES (5° C.)

|  | A(11.0) | B(10.76) | C(10.5) | D(11.0) | E(10.5) | F(10.5) |
|---|---|---|---|---|---|---|
| 0 hours | 0.009 | 0.010 | 0.011 | 0.008 | 0.011 | 0.012 |
| 12 hours | 0.015 | 0.016 | 0.020 | 0.012 | 0.017 | 0.052 |
| 24 hours | 0.051 | 0.021 | 0.026 | 0.016 | 0.022 | 0.073 |
| 48 hours | 0.019 | 0.025 | 0.030 | 0.017 | 0.027 | 0.098 |

TABLE 3

FROZEN SAMPLES (−20° C.)

|  | A(11.0) | B(10.76) | C(10.5) | D(11.0) | E(10.5) | F(10.5) |
|---|---|---|---|---|---|---|
| Initial | 0.009 | 0.010 | 0.011 | 0.008 | 0.011 | 0.012 |
| 24 hours | 0.011 | 0.012 | 0.0175 | 0.010 | 0.012 | 0.022 |
| 48 hours | 0.010 | 0.013 | 0.015 | 0.010 | 0.014 | 0.027 |

No substantial difference in chemical stability was noted between 0 mM, 100 mM, and 150 mM glycine formulations. Solutions with greater glycine concentrations discolored more slowly. Solutions devoid of glycine discolored very quickly regardless of temperature conditions. At 5° C., pH 10.5 to 11 solutions can be held for 24 hours without measurable increases in impurity levels. At room temperature, there is a <0.5% increase in impurities for the pH 11 solution, but at pH 10.5, >1% impurities were measured at 24 hours. Color formation at 5° C. is significantly retarded compared to room temperature. Cold temperatures, i.e., those at or near 5° C., are also preferred for the manufacture of compound 1 and the other compounds of the invention.

EXAMPLE 4
Reduced Glycine Concentration Experiments

Figure 2:
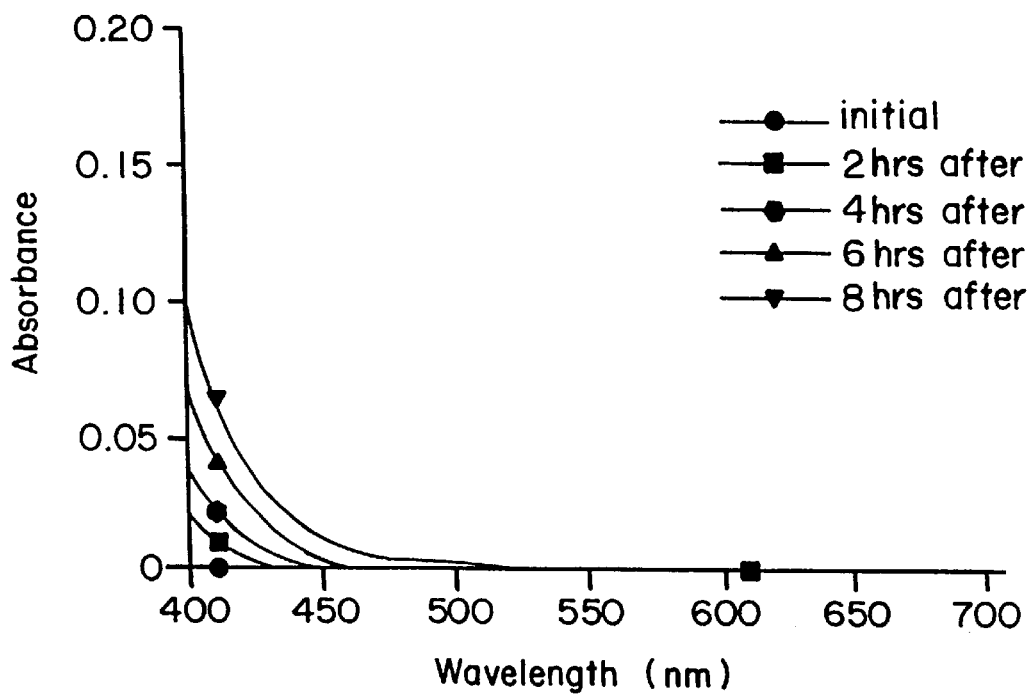
FIG. 2 is a graph showing the changes in absorption spectrum of compound 1 at a concentration of 4 mg/ml in 0.9% saline/50 mM glycine-NaOH buffer at pH 10 as a function of time after dissolution, with storage at room temperature (25° C.) in the dark.

The color change in a 4 mg/ml solution of compound 1 in 0.9% saline at pH 10, with and without 50 mM glycine-NaOH buffer, was evaluated by measurement of absorption at 405 nm as a function of time. 200 mg of compound I was dissolved in 50 ml of 0.9% saline, and was stored at room temperature, i.e., 25° C., in the dark. Absorption measurements were taken at the zero time point, and at 2, 4, 6, and 8 hours after dissolution. As can be seen from FIGS. 1 and 2, compound 1 discolored at a much greater rate in the glycine-free solution than in the solution that contained 50 mM glycine.

Figure 3:
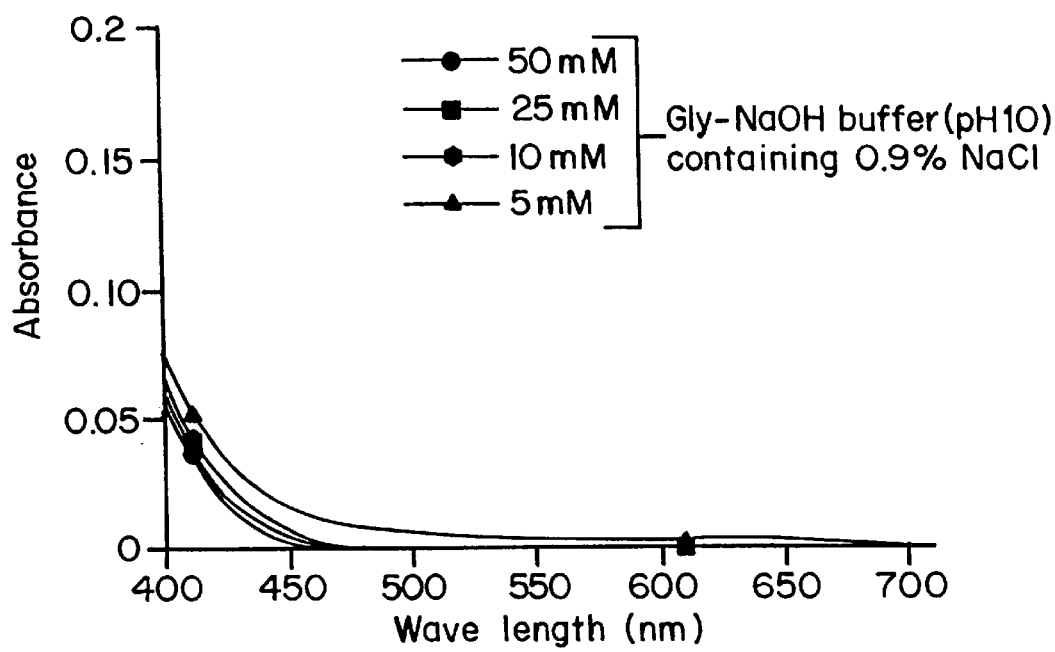
FIG. 3 is a graph showing the change in the absorption spectrum of compound 1, at a concentration of 4 mg/ml, in a solution which contain 5, 10, 25, and 50 mM glycine-NaOH buffer, indicating color change.

The glycine concentration-dependence of compound 1 discoloration was evaluated at 5 hours after dissolution. Compound 1 was dissolved at concentration of 4 mg/ml in 0.9% saline solution at pH 10 containing 5, 10, 25, and 50 mM glycine-NaOH buffer. As can be seen from FIG. 3, at 5 hours post-dissolution, there was little difference in absorbance spectrum between the solutions, although there was a noticeably higher absorbance for the 5 mM glycine-NaOH containing solution.

EXAMPLE 5
Effect of Storage Conditions

Figure 4:
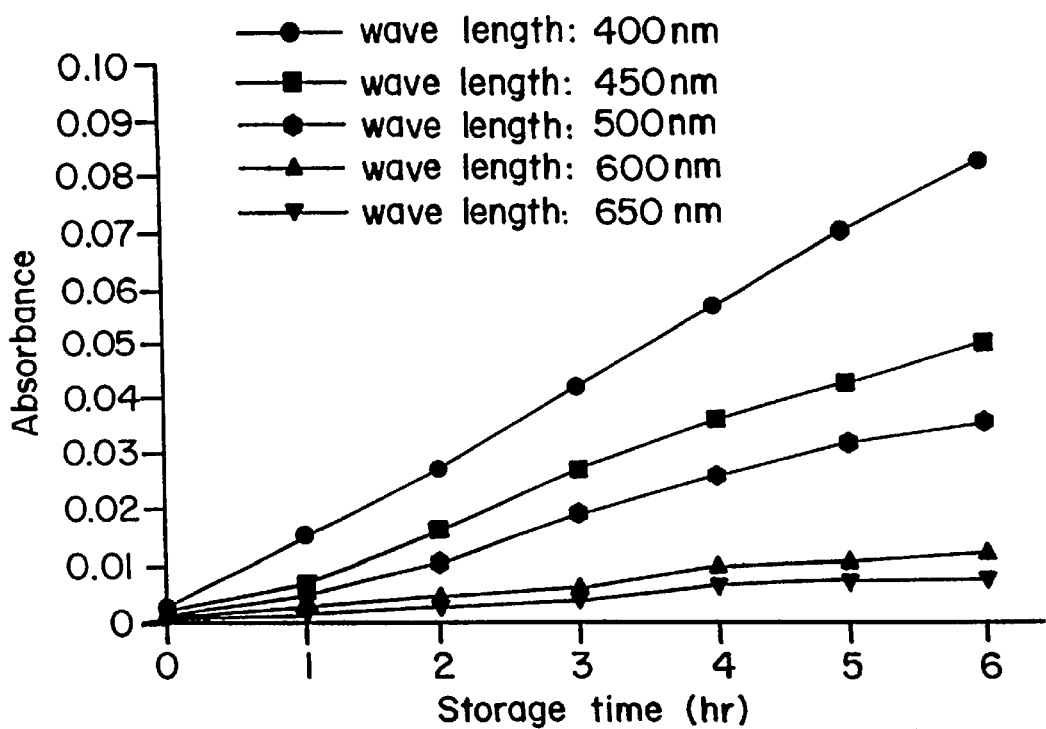
FIG. 4 is a graph showing the change in the absorbance at 400, 450, 500, 550, 600, and 600 nm of compound 1, at a concentration of 2 mg/ml in 0.9% saline, at to room temperature (25° C.) in the light, as a function of time.
Figure 5:
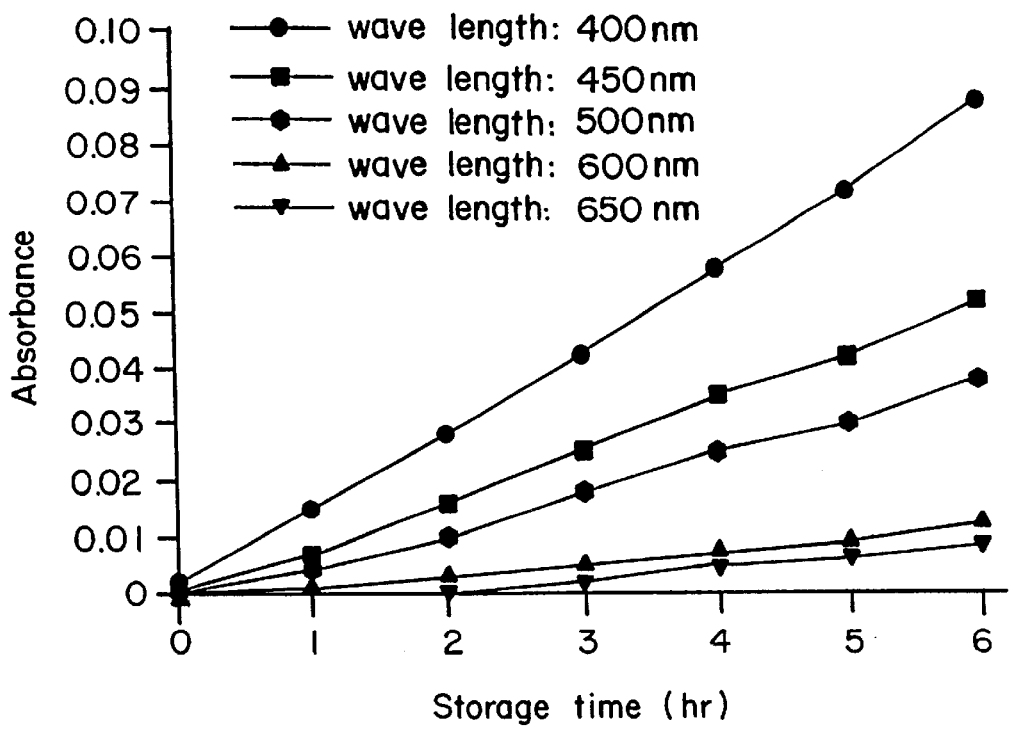
FIG. 5 is a graph showing the change in the absorbance at 400, 450, 500, 550, 600, and 600 nm of compound 1, at a concentration of 2 mg/ml in 0.9% saline, at room temperature (25° C.) in the dark, as a function of time.
Figure 6:
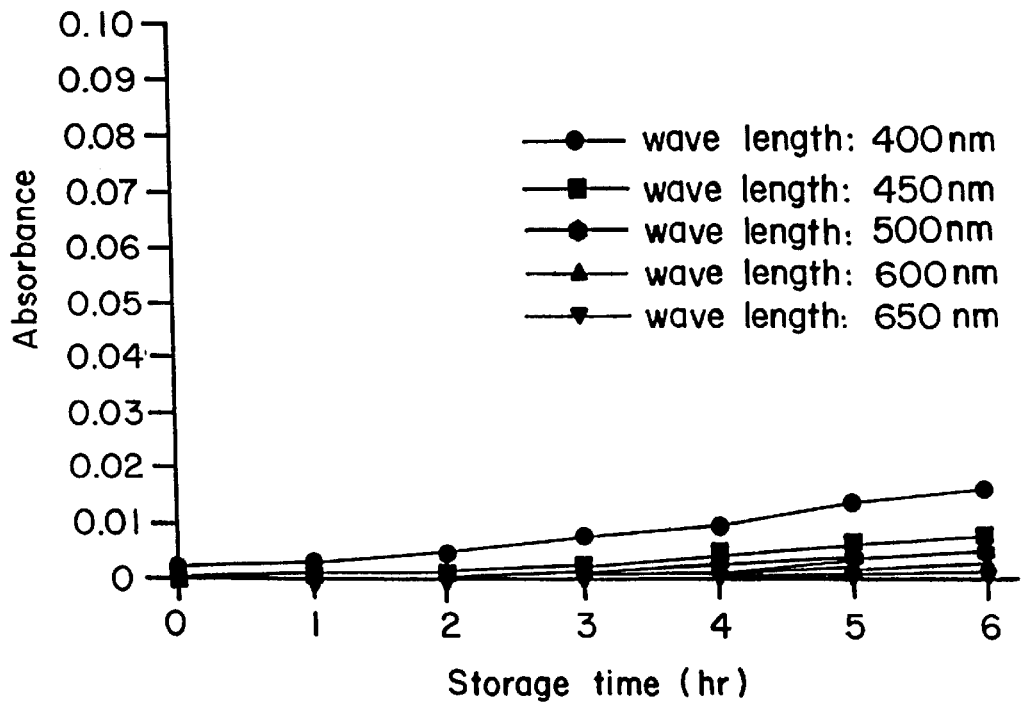
FIG. 6 is a graph showing the change in the absorbance at 400, 450, 500, 550, 600, and 600 im of compound 1, at a concentration of 2 mg/ml in 0.9% saline, at 10° C. in the dark, as a function of time.
Figure 7:
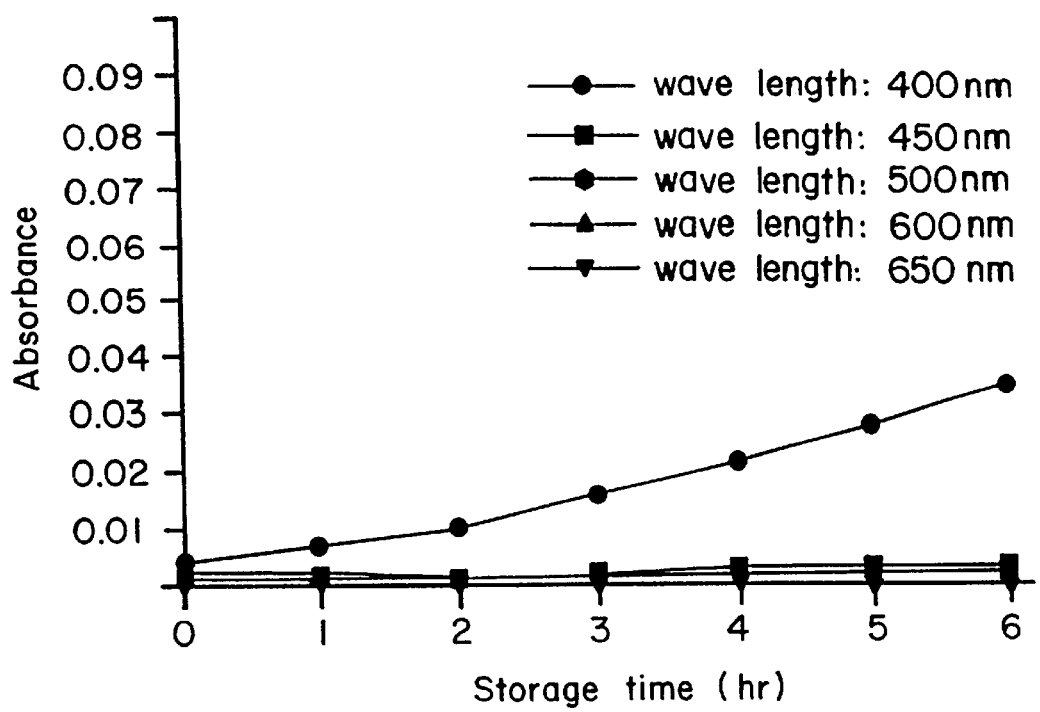
FIG. 7 is a graph showing the change in the absorbance at 400, 450, 500, 550, 600, and 600 nm of compound 1, at a concentration of 2 mg/ml in 0.9% saline and 10 mM glycine-NaOH buffer, at room temperature (25° C.) in the light, as a function of time.
Figure 8:
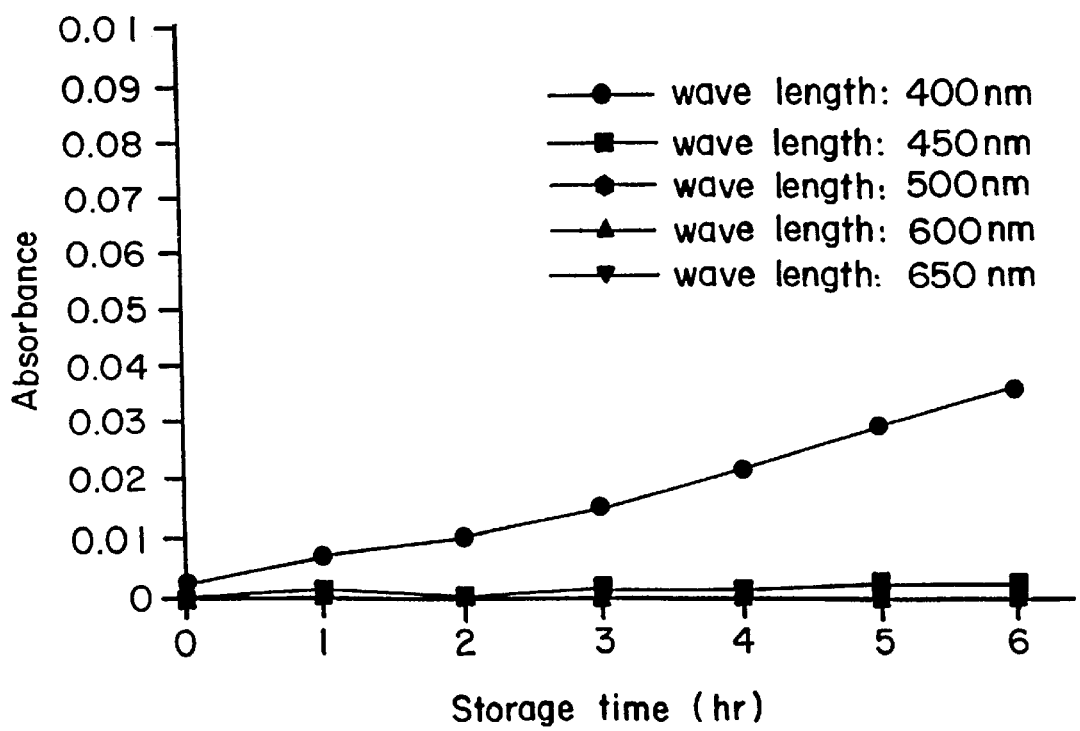
FIG. 8 is a graph showing the change in the absorbance at 400, 450, 500, 550, 600, and 600 nm of compound 1, at a concentration of 2 mg/ml in 0.9% saline and 10 mM glycine-NaOH buffer, at room temperature (25° C.) in the dark, as a function of time.
Figure 9:
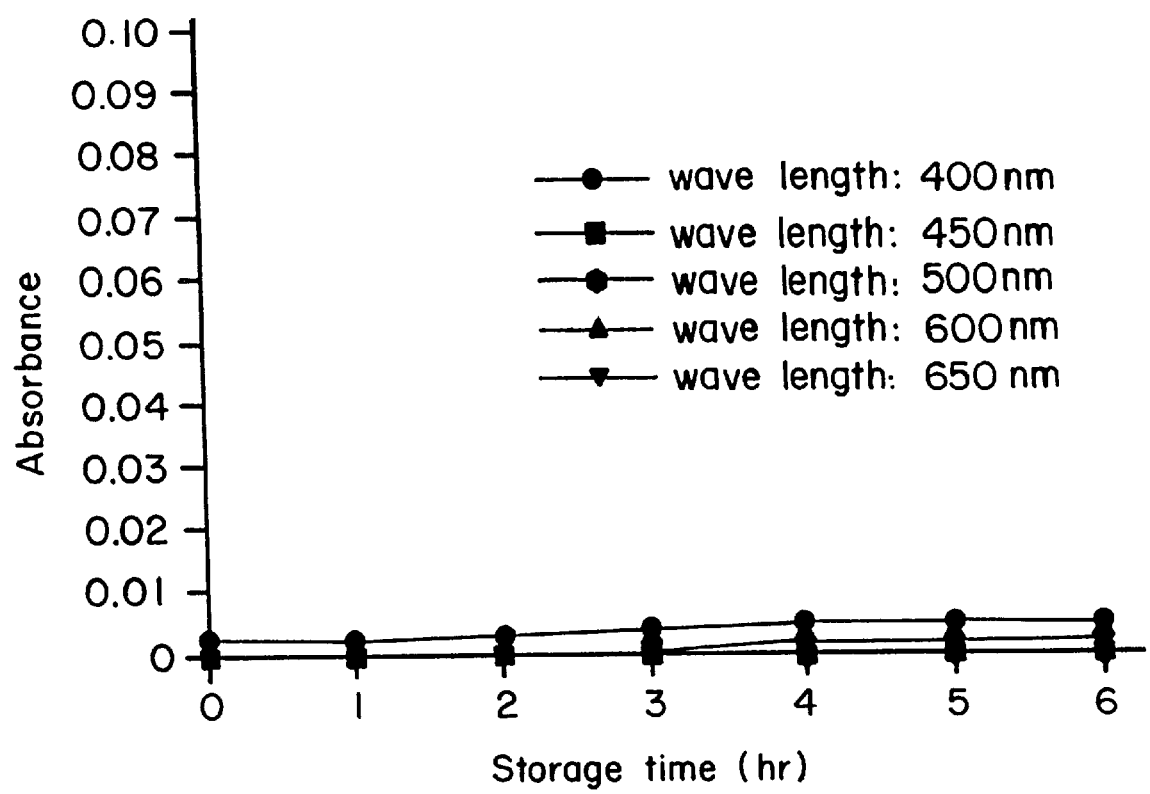
FIG. 9 is a graph showing the change in the absorbance at 400, 450, 500, 550, 600, and 600 nm of compound 1, at a concentration of 2 mg/ml in 0.9% saline and 10 mM glycine-NaOH buffer, at 10° C. in the dark, as a function of time.

The effect of exposure to light and temperature was evaluated as a function of time for 0.9% saline solutions containing 2 mg/ml compound 1, with or without 10 mM glycine-NaOH buffer, was evaluated by monitoring absorbance at 400, 450, 500, 600, and 650 nm. As can be seen from FIGS. 4 to 6, in solutions without glycine-NaOH buffer, increasing storage temperatures caused an increase in undesirable color development. The experiments also reveal that exposure to light has no detrimental effect on color development in solutions containing compound 1. These results are also found with solutions of compound 1 that do contain 10 mM glycine-NaOH buffer. However, as can be seen from FIGS. 7 to 9, the presence of glycine-NaOH buffer decreases absorption at all wavelengths, temperatures, and lighting conditions, i.e., glycine-NaOH buffer reduces color development in solutions of compound 1.

What is claimed is:

1. An intravenous aqueous pharmaceutical formulation comprising:
   a) an anti-ulcerative compound having the following formula:

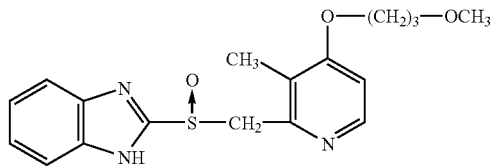

or a pharmaceutically acceptable salt thereof;
   b) glycine; and
   c) a tonicity agent;
   wherein the molecular ratio of glycine to anti-ulcerative compound in between 0.43:1 and 1:1; and
   wherein the formulation is suitable for intravenous administration.

2. The intravenous aqueous pharmaceutical formulation of claim 1, wherein the tonicity agent is selected from the group consisting of sodium chloride and dextrose.

3. The intravenous aqueous pharmaceutical formulation of claim 2, wherein the tonicity agent is sodium chloride and the sodium chloride is present in the formulation at a concentration of about 0.9% by weight.

4. The intravenous aqueous pharmaceutical formulation of claim 2, wherein the tonicity agent is dextrose and the dextrose is present in the formulation at a concentration of about 5% by weight.

5. A lyophilized pharmaceutical formulation comprising:
   a) a) an anti-ulcerative compound having the following formula:

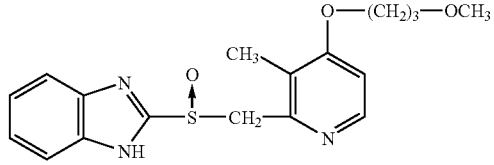

or a pharmaceutically acceptable salt thereof;
   b) glycine; and
   c) NaOH; and
   wherein the molecular ratio of glycine to anti-ulcerative compound is between 0.43:1 and 1:1.

* * * * *